US007973074B2

(12) United States Patent
Demadrille et al.

(10) Patent No.: US 7,973,074 B2
(45) Date of Patent: Jul. 5, 2011

(54) π-CONJUGATED MONO-, OLIGO- AND POLYMERIC COMPOUNDS, AND PHOTOVOLTAIC CELLS COMPRISING THEM

(75) Inventors: Renaud Demadrille, Saint Egreve (FR); Adam Pron, St. Egrève (FR); Muriel Firon, Egly (FR); Jocelyne Leroy, Boullay les Troux (FR)

(73) Assignee: Commissariat a l'Energie Atomique, Paris (FR)

( * ) Notice: Subject to any disclaimer, the term of this patent is extended or adjusted under 35 U.S.C. 154(b) by 941 days.

(21) Appl. No.: 11/587,135

(22) PCT Filed: Apr. 20, 2005

(86) PCT No.: PCT/FR2005/050264
§ 371 (c)(1),
(2), (4) Date: Jul. 16, 2007

(87) PCT Pub. No.: WO2005/105884
PCT Pub. Date: Nov. 10, 2005

(65) Prior Publication Data
US 2007/0289625 A1     Dec. 20, 2007

(30) Foreign Application Priority Data
Apr. 21, 2004  (FR) ..................................... 04 04213

(51) Int. Cl.
*A61K 31/381*   (2006.01)
*C07D 409/14*   (2006.01)
(52) U.S. Cl. .......................................... 514/443; 549/41
(58) Field of Classification Search .................. 514/443; 549/41
See application file for complete search history.

(56) References Cited

U.S. PATENT DOCUMENTS

| 4,390,608 | A | 6/1983 | Hashimoto et al. | |
| 6,872,801 | B2 * | 3/2005 | Ong et al. ..................... | 528/373 |
| 2003/0062536 | A1 | 4/2003 | Heeney et al. | |
| 2003/0081432 | A1 | 5/2003 | Umemoto | |

FOREIGN PATENT DOCUMENTS

| EP | 1 284 258 A2 | 7/2001 |
| EP | 1 327 646 A1 | 7/2003 |
| WO | WO 03/078498 A1 | 9/2003 |

OTHER PUBLICATIONS

Elandaloussi, El Hadj, "Effect of Chain Extension on the Electrochemical and Electronic Properties of π-Conjugated Soluble Thienylenevinylene Oligomers" J. Am. Chem. Soc. 1997, 119, 10774-10784.
Winder, C. et al., "Polymer Solar Cells and Infrared Light Emitting Diodes: Dual Function Low Bandgap Polymer" Molecular Crystals Liquid Crystals, 385, 213-220, 2002.
Wienk M. M. et al., "Efficient Methano [70]fullerene/MDMO-PPV Bulk Heterojunction Photovoltaic Cells" Angew. Chem. Int. Ed., 2003, 42, 3371-3375.
Schilinsky, Pavel et al., "Recombination and Loss Analysis in Polythiophene Based Bulk Heterojunction Photodetectors", Applied Physics Letters, vol. 81, n •20, 3885 (2002).
Gong, Xiong et al. "Stabilized Blue Emission from Polyfluorene-Based Light Emitting Diodes: Elimination of Fluorene Defects", Advanced Functional Material, 13(4), 325-330, 2003.
De Bettignies et al., "Planarized Star-Shaped Oligothiophenes as a New Class of Organic Semiconductors for Heterojunction Solar Cells", Advanced Materials, 2003 15, n•22, pp. 1939-12943.
Edder, Carine et al., "Synthesis of Bridged Oligothiophenes: Toward a New Class of Thiophene-Based Electroactive Surfactants", Org. Letters, 2003, vol. 5, 11, 1879-1882.
Guillerez, S. et al, "New Convenient Synthesis of Highly Regioregular Poly (3-octylthiophene) based on the Suzuki Coupling reaction" Synth. Metals, 1998, 93, 123-126.
Pei, Q. et al., "Poly[3-(4-octylphenyl)thiophene], a New Processible Conducting Polymer" Macromolecules, 1992,25,4297-4301.
Uckert, Frank et al., "A Precursor Route to 2, 7-Poly(9-fluorenone)" Macromolecules, 1999, 32, 4519-4524.
Huynh, Wendy U. et al., "Hybrid Nanorod-Polymer Solar Cells" Science, vol. 295, Mar. 2002.

* cited by examiner

*Primary Examiner* — Taofiq A Solola
(74) *Attorney, Agent, or Firm* — McKenna Long & Aldridge LLP

(57) ABSTRACT

Monomeric, oligomeric or polymeric compound corresponding to the following formula (I):

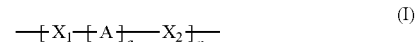

in which:
A represents an optionally substituted polycyclic group, the said polycyclic group comprising at least one group capable of making possible the attachment of a chromophoric group,
$X_1$ and $X_2$, which are identical or different, each independently represent a group of formula (II):

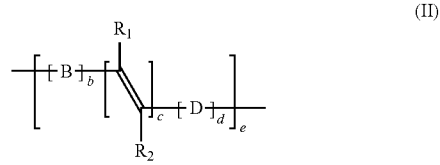

in which:
B and D, which are identical or different, each independently represent an aromatic carbon ring or an aromatic heterocycle which is optionally substituted.
Use of the said compound in an optoelectronic device, such as a photovoltaic cell, a field-effect transistor or an electrochemical sensor.
Photovoltaic cell comprising an active layer comprising an electron donor composed of the said compound.

17 Claims, 3 Drawing Sheets

π-CONJUGATED MONO-, OLIGO- AND POLYMERIC COMPOUNDS, AND PHOTOVOLTAIC CELLS COMPRISING THEM

This application is claims priority to International Patent Application No. PCT/FR2005/050264, filed on Apr. 20, 2005, which claims priority to French Patent Application No. 04 04213, filed on Apr. 21, 2004, all of which are hereby incorporated by reference, as if fully set forth herein.

TECHNICAL FIELD

The invention relates to novel π-conjugated mono-, oligo- and polymeric compounds. In particular, the invention relates to novel compounds comprising at least one unit with a fluorenone structure or a derivative of the latter and optionally thienylene-vinylene units.

The invention also relates to the use of these compounds in optoelectronic devices and to the photovoltaic cells comprising these compounds.

The technical field of the invention may be defined as that of organic semiconductors and in particular heterojunctions.

A large number of applications of organic semiconductors relate to their use in electronic systems, such as electroluminescent diodes, field-effect transistors or photovoltaic cells. The latter application of organic semiconductors is based on the ability of certain π-conjugated polymers and oligomers, or also small π-conjugated molecules, to convert light energy to electrical energy.

When a junction is formed composed of two semiconductors of different natures, at least one of which is organic, a heterojunction is thus defined.

The mixtures as an anisotype hetero-junction, that is to say between an organic semi-conductor of p type and an organic or inorganic semiconductor of n type, have had numerous applications in recent years in the field of plastic electronics, for example in electroluminescent diodes and photovoltaic cells. Generally, in the latter, the π-conjugated polymer or oligomer or the small π-conjugated molecule mentioned above is brought into contact with an acceptor of n type, such as fullerene or a derivative of the latter, and it acts as donor of p type.

Under light irradiation, an electron-hole pair is created (exciton) on the π-conjugated monomer, oligomer or polymer. This exciton is dissociated by capture of the electron by the acceptor. These charges are collected at the electrodes and generate a current.

Heterojunctions in the photovoltaic field are disclosed in particular in the document WO-A-03/078498, which relates to conjugated polymers derived from PolyPhenyleneVinylene (PPV). These electrically conducting polymers are used in particular in the active layers of photovoltaic cells.

One of the major problems of these cells relates to the absorption of light; this is because, in order to be efficient, the absorption spectrum of the polymer or of the oligomer should be as close as possible to the emission spectrum of the sun. The more efficient the absorption of light, the greater the possibility of creating excitons. In the case of PPV and its derivatives, the absorption region does not exceed 650 nm in the solid state.

In order to solve this problem, attempts have been made to increase the absorption region of the active layer by using low gap polymers, for example based on thienylpyrrole and on benzodithiazole, as is described in the document "Molecular Crystals Liquid Crystals", 385, 213-220, 2002, or else by using methano[70]fullerene derivatives which absorb more distantly in the visible region, as is mentioned in the paper "Efficient Methano[70]fullerene/MDMO-PPV Bulk Heterojunction Photovoltaic Cells" by M. M. WIENK et al., Angew. Chem. Int. Ed., 2003, 42, 3371-3375.

Another family of polymers has recently been studied: it is the family of the poly(alkylthiophene)s. Thus, the paper in Applied Physics Letters, Vol. 81, No. 20, p. 3885 (2002), describes heterojunctions comprising a mixture of poly(3-hexylthiophene) and of a methanofullerene.

Poly(alkylthiophene)s have also been studied as a mixture with inorganic CdSe-type semiconductor nanocrystals in the paper "Hybrid Nanorod-Polymer Solar Cells" by W. U. HUYNH et al. in Science, Vol. 295, March 2002.

In the case of the use of the poly(alkylthiophene)s, only the regioregular polymers are used, for reasons of mobility of the charges. This is because the transportation of the charges is another critical point in these devices.

The regioregularity favours the self-organization and makes it possible to increase the degree of crystallinity of the materials, which is favourable to the electrical transportation. In addition, it should be noted that regioregular poly(alkylthiophene)s also exhibit broader absorption regions than random poly(alkylthiophene)s.

Furthermore, fluorene derivatives are also materials known for their good optoelectronic properties. Thus, the document EP-A2 1 284 258 disclosed in the use of mono-, oligo- and polyalkylidenefluorene compounds as transporters of charges in electrical devices, such as field-effect transistors, electroluminescent diodes, photovoltaic cells and sensors.

The semiconducting organic polymers disclosed in the documents of the prior art exhibit an absorption region which is not sufficiently close to the emission spectrum of the sun and which does not extend sufficiently into the visible region. In addition, the generation and the dissociation of the excitons is inadequate, which may be the cause of an excessively low mobility of the charge carriers and of an excessively low transportation to the electrodes.

There thus exists a need for compounds or a material and in particular for a semiconducting organic monomer, oligomer or polymer, the absorption region of which is greatly extended into the emission spectrum of the sun, which generates a large amount of excitons and in any case more excitons than in the compounds, for example the polymers, of the prior art.

The aim of the present invention is to provide a semiconducting organic compound, in particular for photovoltaic cells, which meets, inter alia, these needs.

Another aim of the present invention is to provide a semiconducting organic compound, in particular for photovoltaic cells, which does not exhibit the disadvantages, failings, limitations and drawbacks of the compounds of the prior art and which solves the problems of the prior art.

This aim and yet others are achieved, in accordance with the invention, by monomeric, oligomeric and polymeric compounds corresponding to the following formula (I):

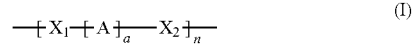

in which
A represents a polycyclic group optionally substituted by one or more identical or different R groups chosen from alkyl radicals, the said polycyclic group comprising at least two rings chosen from aromatic carbon rings and/ or aromatic heterocycles and comprising at least one group capable of making possible the attachment of a chromophoric group, $X_1$ and $X_2$, which are identical or different, each independently represent a group of formula (II):

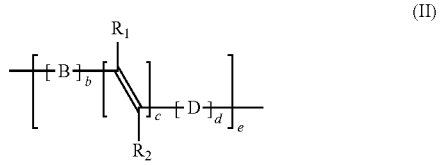

(II)

in which

B and D, which are identical or different, each independently represent an aromatic carbon ring or an aromatic heterocycle optionally substituted by one or more R groups;

$R_1$ and $R_2$, which are identical or different, each independently represent a group chosen from the hydrogen atom, R groups, the cyano group, the nitro group, halogen atoms and deuterium atoms;

b and d are integers from 0 to 100, preferably from 0 to 12, including all the values between 0 and 12;

c is an integer from 0 to 20, preferably from 0 to 5, including all the values between 0 and 5;

e is an integer from 0 to 100, preferably from 0 to 10, including all the values between 0 and 10;

$X_1$ and/or $X_2$ are optionally substituted by one or more groups of formula (II) identical to or different from the substituted $X_1$ or $X_2$ group;

n is an integer from 1 to 1000, preferably from 1 to 200, including all the values between 1 and 200;

a is an integer from 1 to 100, preferably from 1 to 5, including all the values between 1 and 5;

one or more of the hydrogen atoms of the formula (I) can be replaced by a deuterium or fluorine atom.

The compound according to the invention can be a monomer (n=1).

This monomer can be symmetrical or asymmetrical but is preferably symmetrical; this is because regioregular alternating oligomers and polymers devoid of coupling defects can be obtained from these symmetrical monomers by homopolymerization.

The term "symmetrical" is understood to mean generally that $X_1$ is identical to $X_2$ in the formula (I).

Advantageously, the group capable of making possible the attachment of a chromophoric group is a group

where X represents O, S, Se or N—$R_3$, $R_3$ being chosen from the groups resulting from the reaction of a carbonyl group (X=O) with an amine to form an imine bond.

The carbonyl group (X=O) can be modified by reaction with any amine to form an imine bond. Preferably, this imine is chosen from aniline and the derivatives of the latter or aniline oligomers and the derivatives of the latter and again preferably this amine is the aniline tetramer in the emeraldine base form.

Advantageously, in the formula (I), the polycyclic group of the A group is a condensed polycyclic group rather than a polycyclic group comprising several rings bonded via single bonds or bonding groups.

Advantageously, in the formula (I), the A group is chosen from fluorenone, truxenone, indenofluorenone, benzofluorenone, dibenzofluorenone, indenofluorenedione, cyclopentafluorenone, cyclopenta-fluorenedione, thiopyranone, phenanthrenone or cyclopentadithiophenone groups and the groups derived from these (derivatives of the groups listed below); groups derived from xanthone of formula

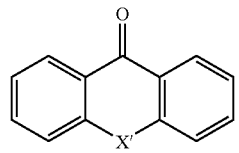

where X' represents a —CO—, —S—, —Se—, —NH—, —CH$_2$— or —CH$_2$=CH$_2$— radical; groups derived from 4-piperidone comprising at least two condensed aromatic carbon rings and/or aromatic heterocycles, these groups optionally being substituted by one or more R groups and/or optionally condensed with one or more aromatic carbon rings and/or aromatic heterocycles.

Furthermore, the oligomers and polymers according to the invention may comprise A groups of the same nature or of different nature.

The oligomers and polymers are preferably regioregular oligomers and polymers which preferably comprise a single type of A group, which are devoid of coupling defects and which are obtained from the above symmetrical monomers.

The regioregular polymers can be obtained without coupling defects even with a high molecular weight, namely generally of 2000 to 200 000 Da.

Preferably, in the formula (II), B and D represent a thiophene group, preferably a thien-2,5-diyl group.

Preferably, B and D both represent such a group.

Preferably, B and D, in particular when they represent a thiophene as defined above, are substituted by an alkyl radical of 1 to 10 carbon atoms, such as the n-octyl radical.

This is because it turned out that, when the B and D units of thienylene type, for example, carry alkyl groups, the solubility of the system is increased, which allows use by the liquid route.

It should be noted that the attachment of the B and D rings and the position of the R and $R_1$ and $R_2$ substituent or substituents is preferably chosen to obtain a symmetry of the molecule in the case of a monomer, such a symmetry of the monomer subsequently resulting in regioregular alternating polymers.

Preferably, the A group is a fluorenone group or derivative thereof and it corresponds to the following formula:

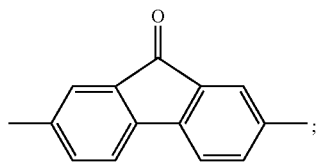

and $X_1$ and $X_2$, which are identical or different, correspond to the following formula:

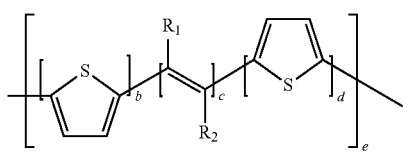

it being possible for the A group and the thienyl groups optionally to be substituted by one or more R groups.

A particularly preferred compound according to the invention corresponds to the following formula:

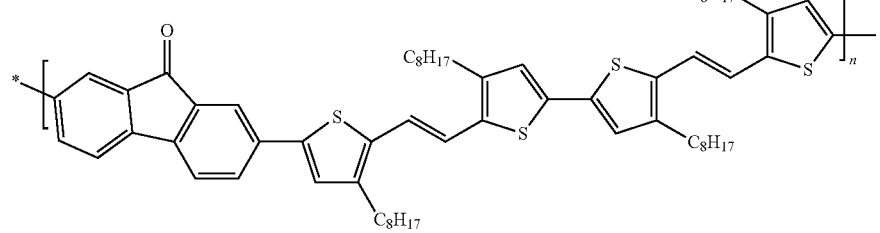

This compound is 2,7-bis(5-[(E)-1,2-bis(3-octylthien-2-yl) ethylene])-fluoren-9-one (TVF) if n=1 (monomer); or poly(2,7-bis(5-[(E)-1,2-bis(3-octylthien-2-yl)ethylene])-fluoren-9-one) (poly(TVF)) if n is greater than 1 (oligomer or polymer).

In the above formulae (I) and (II), the term "alkyl" used for the alkyl radicals and for the groups comprising an alkyl part means, unless otherwise indicated, a linear or branched carbon chain comprising from 1 to 30 carbon atoms, preferably from 1 to 10, better still from 1 to 8, which can comprise one or more carbon-carbon double bonds or triple bonds and/or which can be carried and/or interrupted by one or more oxygen, sulphur, silicon or nitrogen atoms and/or which can be substituted by one or more groups chosen from halogen atoms, such as chlorine, bromine, iodine and fluorine; heterocycles; or aryl, hydroxyl, alkoxy, amino, acyl, carboxamido, —$CO_2H$, —$SO_3H$, —$PO_3H_2$, —$PO_4H_2$, —$NHSO_3H$, sulphonamido, monoalkylamino or trialkyl-ammonio radicals; or alternatively by a dialkylamino radical in which the two alkyl groups can form, in conjunction with the nitrogen atom of the said di($C_1$-$C_4$)alkylamino group to which they are bonded, a ring which can be interrupted by one or more nitrogen, oxygen or sulphur atoms.

Likewise, according to the invention, the term "alkoxy" used for the alkoxy radicals and for the groups comprising an alkoxy part means, unless otherwise indicated, an O-alkyl chain, the term "alkyl" having the meaning indicated above. The alkoxy radicals of the alkoxycarbonyl groups preferably have from 1 to 4 carbon atoms. The acyl groups are preferably of 2 to 4 carbon atoms.

According to the invention, the term "heterocycle" is understood to mean an aromatic (when this is specified) or nonaromatic ring comprising 5, 6 or 7 members and from 1 to 3 heteroatoms chosen from nitrogen, sulphur and oxygen atoms. These heterocycles can be condensed with other heterocycles or with other rings, in particular aromatic rings, such as a phenyl group. In addition, these heterocycles can be quaternized by an alkyl radical. The term "alkyl" and the term "alkoxy" have the meanings indicated above.

Mention may in particular be made, among the heterocycles and in particular those of B and D, by way of example, of the following rings: thiophene, benzothiophene, furan, benzofuran, indole, indoline, carbazole, pyridine, dehydroquinoline, chromone, julodinine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine or aziridine.

According to the invention, the term "aromatic carbon ring" is understood to mean, unless otherwise specified, a $C_6$ to $C_{30}$ aryl radical which can be substituted by one or more of the following radicals: alkyl; alcoxy; acyl; cyano; carboxamido; —$CO_2H$; —$SO_3H$; —$PO_3H_2$; —$PO_4H_2$; hydroxyl; amino; mono($C_1$-$C_4$)alkylamino; or di($C_1$-$C_4$)alkylamino; in which the two alkyl groups can form, in conjunction with the nitrogen atom of the said di($C_1$-$C_4$)alkylamino group. Preferably, the aryl group is a phenyl group or a naphthyl group which can be substituted as indicated above.

The invention also relates to the use of the compound as described above in an optoelectronic device, such as a photovoltaic cell, a field-effect transistor or an electrochemical sensor.

The invention also relates to a photo-voltaic cell comprising an active layer comprising an electron donor composed of the compound as described above and an electron acceptor.

The said electron acceptor is generally chosen from organic acceptors, such as PCBM (1-(3-methoxycarbonyl) propyl-1-phenyl-[6,6]-C61), $C_{60}$ derivatives, $C_{70}$ derivatives, carbon nanotubes, perylene, tetracyanoquinodimethane (TCNQ) and quinoxalines; and inorganic acceptors, such as semiconductor nanocrystals, which may or may not be coated by an organic layer.

Fluorene derivatives are compounds known for their good optoelectronic properties, as is disclosed, for example, in the document EP-A2-1 284 258 already mentioned above.

However, this document does not disclose any fluorenone monomer, oligomer or polymer.

Polymers comprising fluorenones have been very little studied. The documents relating to these compounds in the context of optoelectronic devices indicate that fluorenones are regarded as decomposition products of polyfluorenes. The presence of fluorenone is not in fact desirable in optoelectronic devices as the fluorenones modify in an uncontrollable way the emission colours of electroluminescent diodes, as is mentioned in the document Advanced Functional Materials, 13(4), 325-330, 2003.

The materials comprising fluorenone units have never been mentioned in the context of use in photovoltaic cells or in field-effect transistors.

The preparation of the fluorenone compounds according to the invention for the purpose of their use in photovoltaic cells and field-effect transistors thus goes against a widespread preconception in this technical field and overcomes this preconception.

Thus, the document US-2003/00 81432 A1 relates to a process for the preparation of polymers comprising cyclopentanone structures, for example of a poly(9-fluorenone) polymer, and to the use of these polymers in electroluminescent diodes (ELD). This document is prior to the document "Advanced Functional Materials" of 2003 mentioned above, which places the emphasis on the serious drawbacks caused by these polymers in ELDs. In addition, this document neither mentions nor suggests that the polymers which are prepared therein can be used in photovoltaic cells and field-effect transistors.

It is clear that the polymers prepared in the abovementioned document are not under any circumstances suitable for use in field-effect transistors and photovoltaic cells and that their properties with regard to absorption region, generation of excitons, mobility of the charges and solubility are insufficient and are not suitable for use in these devices.

The materials according to the invention, whether monomers, oligomers or polymers, are fundamentally defined by a structure, a π-conjugated architecture, which comprises several types of chromophore, namely, generally, on the one hand, the chromophores present in the A groups, which are preferably fluorenones or derivatives of the latter, and, on the other hand, the chromophores present in the $X_1$ and/or $X_2$ groups, which are preferably thienylene-vinylene units.

The presence of several types of chromophores extends the absorption spectrum of the compounds of the invention into the visible part of the spectrum and also improves the collecting of the photons, and consequently also promotes the generation of the excitons and makes it possible to generate more excitons than in the compounds of the prior art which do not have the specific structure of the compounds according to the invention.

Furthermore, the structure of the compounds according to the invention has proved to be very effective in the context of the conversion of the photons to electrons, as is shown in FIG. 3.

As regards the polymers according to the invention, their π-conjugated macromolecular architecture is preferably chemically well defined, with controlled regioregularity, and as flat as possible. This approach makes it possible to obtain polymers with a self-organization which is favoured and a crystallinity which is optimized. Consequently, the mobility of the charges in the materials of the invention is enhanced.

The monomers, oligomers and polymers according to the invention do not exhibit the disadvantages of the compounds of the prior art and introduce a solution to the problems of the compounds of the prior art.

Moreover, in addition to responding to the problems posed, the compounds according to the invention, due to their specific structure, are highly adaptable, making it possible to refine the properties desired.

In particular, the compounds according to the invention comprise, in the A group, at least one group capable of making possible the attachment of a chromophoric group (additional chromophoric group which will supplement the chromophoric groups already present in the A, $X_1$ and $X_2$ groups).

This group which makes possible the attachment of a chromophore, such as a carbonyl group, by which the compounds according to the invention are provided makes it possible to introduce other chromophores in the side position. This is because this group, such as a carbonyl group, is sufficiently reactive to make possible such an introduction but also sufficiently stable to prevent decomposition during the polymerization stage.

In other words, the compounds according to the invention, in particular the polymers according to the invention, can be fundamentally distinguished by their structure from the compounds disclosed in the documents of the prior art represented, for example, by the document WO-A1-03/078498.

The polymers according to the invention exhibit a broader absorption region in the visible part of the solar spectrum due to the presence of several chromophores and thus make it possible to collect more photons in this zone. Consequently, the compounds according to the invention make it possible to generate more excitons (see FIG. 1).

This clearly emerges from FIG. 1, where the solid state spectra, with a film of the same thickness deposited on glass, of a PCBM/MDMO-PPV mixture of the prior art not in accordance with the invention and of a PCBM/PTVF mixture which involves a polymer (PTVF) according to the invention are compared.

The monomers of the invention, such as TVF, can also be distinguished from the prior art as they can be employed in solution, like the polymers.

In the prior art, the small organic molecules used in photovoltaic cells are all made use of by sublimation, as is described, for example, in the document Advanced Materials, 2003, 15, No. 22, pages 1939-1943.

The invention will be better understood on reading the description which will follow, given by way of illustration and without implied limitation, with reference to the appended drawings, in which:

FIG. 1 is a graph which represents the solid state spectra, for films with the same thickness deposited on glass, respectively of a PCBM/MDMO-PPV mixture not in accordance with the invention (dotted line curve) and of a PCBM/PTVF mixture in accordance with the invention (solid line curve).

The optical density (O.D.) is carried on the ordinate and the absorption wavelength λ (in nm) is carried on the abscissa.

The absorption spectrum of the active layer (solid line curve) is carried on the same graph.

The wavelength λ (in nm) is carried on the abscissa and the IPCE (%) (left hand side) and the optical density O.D. or absorption (right hand side) are carried on the ordinate.

Figure 4:
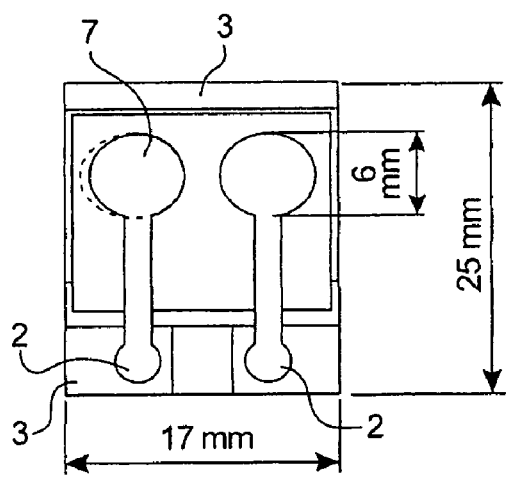

FIG. 4 is a diagrammatic view taken from above of a photovoltaic cell.

Figure 5:
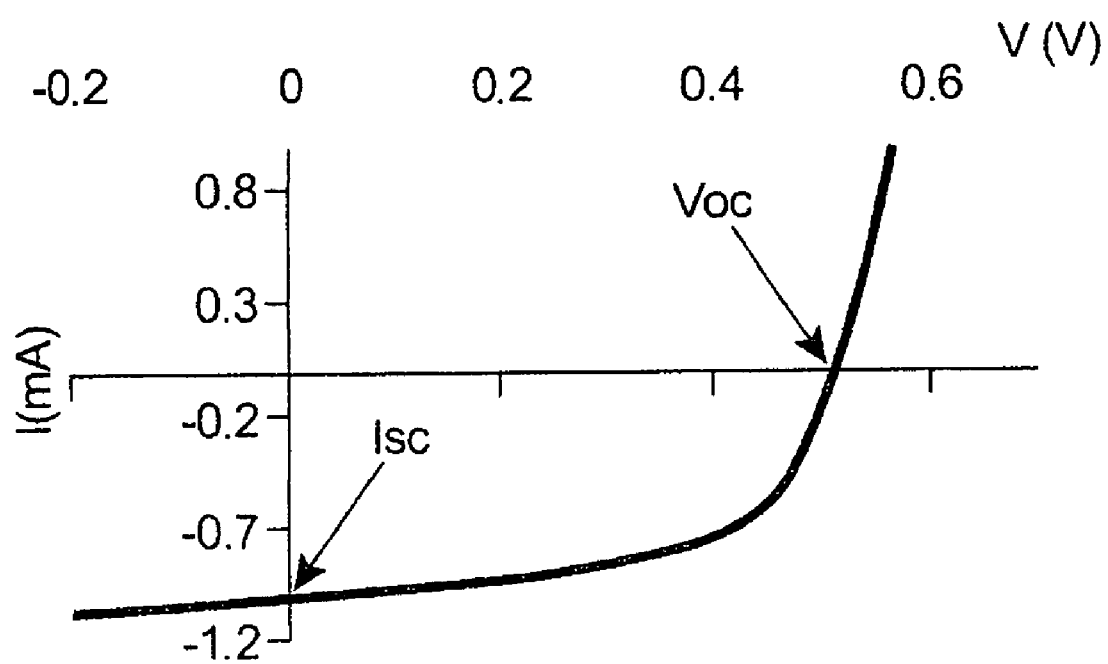

FIG. 5 is a graph which represents the I(V) curve of a cell comprising a PCBM/PTVF mixture according to the invention in the active layer.

The voltage V (volts) is carried on the abscissa and the current strength I (mA) is carried on the ordinate.

The description which follows is made essentially with reference to the preparation and to the use of a symmetrical monomer which is TVF, namely 2,7-bis(5-[(E)-1,2-bis(3-octylthien-2-yl)ethylene])-fluoren-9-one, and to the preparation and use of a defect-free regioregular alternating PTVF polymer from this precursor monomer, but it is very obvious that this description can be applied to all the monomers, oligomers and polymers of formula (I) according to the invention with the necessary adaptations of the processes and means for implementation which can be easily carried out by a person skilled in the art in this technical field.

The synthetic approach for accessing the symmetrical monomers according to the invention of formula (I) can be described in the following way as regards TVF:

Firstly:

A thienylene-vinylene derivative, such as (TV) (E)-1,2-bis (3-octylthien-2-yl)ethylene, is prepared according to a method described in the publication J. Am. Chem. Soc., 1997, Vol. 119, p. 10774. This derivative is functionalized by a boronic ester or a stannyl group according to known procedures, such as those described, for example, in Org. Letters, 2003, Vol. 5, 11, 1879-1882 and in Synth. Metals, 1998, 93, 123-126. These functional groups are known to be effective in palladium-catalysed couplings.

The derivatives thus functionalized can then be coupled to 2,7-dibromofluorenone, which is a commercial product, using the Stille or Suzuki coupling conditions well known to a person skilled in the art.

A symmetrical monomer, such as TVF, is thus obtained which can then, if desired, be homopolymerized by various methods.

A first method is chemical or electro-chemical oxidizing coupling, for example using ferric chloride ($FeCl_3$), as is described, for example, in Macromolecules, 1992, 25, 4297-4301.

A second method is the polycondensation or polyaddition of correctly functionalized derivatives of the monomers, such as TVF, for example, by incorporating bromines in the α position of the end thiophenes. It is then possible to use the Yamamoto coupling conditions, the polymerization taking place by polyaddition in the presence of a "zero valent" nickel complex. Such a process is described, for example, in Macromolecules, 1999, 32, 4519-4524.

However, it is possible to envisage other methods for the preparation of the polymers, in particular by a copolymerization reaction between a disubstituted thienylene or vinylidene derivative and a disubstituted fluorenone derivative. However, yet other methods can also be used.

The compounds according to the invention can be used in all kinds of optoelectronic devices, such as photovoltaic cells, field-effect transistors and electrochemical sensors.

Figure 2:
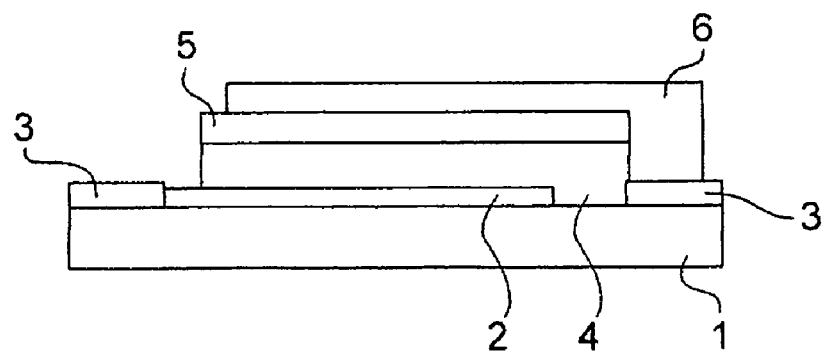
FIG. 2 is a diagrammatic view in vertical cross section of a photovoltaic cell exhibiting an active layer which can comprise the compounds according to the invention.

A representation has been given, in FIGS. 2 and 4, of a photovoltaic cell which comprises an active layer in which a mono-, oligo- or polymeric compound according to the invention, mixed with an acceptor, is incorporated (FIGS. 2 and 4 are respectively the side view and the top view).

This cell is manufactured on a transparent substrate (1) made of a material which can be flexible or stiff, for example glass, and on which a conducting layer (2), composed of metal oxide, for example of indium tin oxide (ITO), is found deposited.

The ITO film (2) is etched, for example over a third of the surface. The sample is subsequently cleaned ultrasonically in various solutions: preferably acetone and then ethanol. It is subsequently rinsed with deionized water, with TDF4, then it is rinsed and dried in an oven.

Chromium/gold contacts (3) are deposited under vacuum in order to make it possible to subsequently measure the I (V) characteristic of the cell. A pre-layer (4), which can be polyaniline in the conductive state or PEDOT (poly(ethylenedioxythiophene)) doped with PSS (polystyrenesulphonate), is deposited on this substrate. The thickness of this "pre-layer" (4) is generally between 10 and 150 nm but it is preferably 80 nm.

The active organic layer (5) composed of the conjugated electron donor according to the invention in its mono-, oligo- or polymeric form, mixed with the acceptor, preferably PCBM (1- (3-methoxycarbonyl)propyl-1-phenyl-[6,6]-C61), which is a soluble fullerene derivative, is deposited by the liquid route directly on this "pre-layer" described above.

As regards the acceptor used in the active layer, it should be noted that PCBM can be replaced by any other acceptor of organic type exhibiting equivalent energy levels, such as $C_{60}$ derivatives, and also $C_{70}$ derivatives, carbon nanotubes, perylene, tetracyanoquinodimethane (TCNQ) or quinoxalines. PCBM can also be replaced by any inorganic acceptor exhibiting the same characteristics, such as semi-conductor nanocrystals, which may or may not be coated with an organic layer.

For the deposition of the active layer (5), the donor and the acceptor are in solution in an organic solvent or a combination of organic solvents.

These solvents can be aliphatic, aromatic or heteroaromatic and substituted or unsubstituted. More particularly, these solvents are nonpolar aromatic solvents and can be chosen, for example, from toluene, ortho-dichlorobenzene, chlorobenzene and their mixtures. Chlorobenzene is the preferred solvent.

The concentration of the acceptor is generally between 0.1 and 100 g/l and it is preferably 10 g/l and the concentration of the donor is generally between 0.1 and 100 g/l and it is preferably 8.75 g/l.

The electrode is composed of a film (6), generally of LiF, with a thickness generally of 0.5 to 5 nm, preferably 1.3 nm, deposited, for example under vacuum, on the active layer (5) and of a layer, for example of aluminium, for example deposited under vacuum, of 5 to 200 nm but preferably 70 nm which will cover this LiF film.

An illuminated surface (7), generally circular, with a diameter, for example of 6 mm, is defined on this layer, for example of Al.

The photovoltaic cell generally has the shape of a rectangle with, for example, a width of 17 mm and a length of 25 mm.

The invention will now be described with reference to the following examples, given by way of illustration and without implied limitation.

EXAMPLE 1

In this example, the synthesis is carried out of the monomer TVF (namely, 2,7-bis(5-[(E)-1,2-bis(3-octylthien-2-yl) ethylene]) -fluoren-9-one) according to the invention.

Reactants and Chemicals

All the reactants and chemicals were acquired from Aldrich.

The THF was distilled over sodium/benzo-phenone before use.

The other reactants and chemicals were used as received.

Characterization Techniques

Thin layer chromatography was carried out on thin layer chromatography sheets, silica gel on aluminium support, size 2 to 25 μm, pore size 60 Å. The silica used for the flash chromatography is Merck®60 (70-230 mesh). All the molecules synthesized were characterized by $^1H$ and $^{13}C$ NMR and elemental analysis.

The NMR spectra were recorded on a Brucker®AC 200 MHz or Varian® 400 MHz spectrometer. d-Chloroform, $d_6$-acetone or $d_6$-DMSO comprising TMS as internal standard were used as solvent depending on the solubility of the material.

The elemental analyses were carried out by the analytical department of the CNRS at Vernaison (France).

Synthesis of the Precursors

General procedure for the preparation of the dioxaborinane precursor:

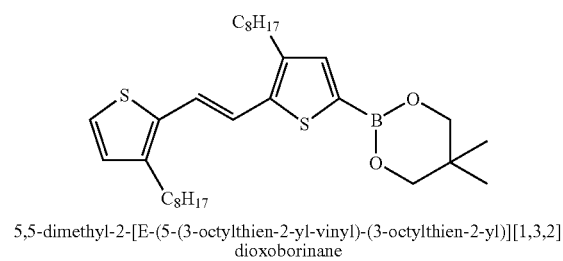

5,5-dimethyl-2-[E-(5-(3-octylthien-2-yl-vinyl)-(3-octylthien-2-yl)][1,3,2]dioxoborinane 1.46 ml (2.33 mmol) of n-butyllithium in the form of 1.6M solution in hexane were added dropwise, at −50° C., over 5 minutes to a stirred solution of 884 mg (2.12 mmol) of (E)-1,2-bis(3-octylthien-2-yl)ethylene in dry THF (15 ml).

This mixture was stirred for a further 60 minutes at −50° C. and then cooled to −78° C. At this stage, 1.72 ml (6.38 mmol) of tributyl borate were rapidly added to the reactor and the solution was allowed to warm up again to ambient temperature.

While warming up, the reactive mixture became milky. It was then poured into 1M HCl comprising ice (40 ml) and then extracted with ethyl ether. The organic phase was washed twice with sodium chloride solution and dried for 30 minutes over magnesium sulphate in the presence of 5.20 g (50 mmol) of neopentyl, glycol. The subsequent separation of the drying agent by filtration and the removal of the solvent using a rotary evaporator gave an orange oil.

Very thorough purification by silica gel column chromatography with a hexane/ether (9:1) mixture as eluent gave 5,5-dimethyl-2-[E-(5-(3-octylthien-2-yl-vinyl)-(3-octylthien-2-yl)][1,3,2]dioxoborinane. Viscous orange oil (yield: 61%).

$^1$H NMR (CDCl$_3$, 200 MHz, ppm): δ: 7.24 (s, 1H), 7.05 (d, 1H, J=15.6 Hz), 7.00 (d, 1H, J=4.8 Hz), 6.90 (d, 1H, J=15.8 Hz), 6.76 (d, 1H, J=5.4 Hz), 3.69 (s, 4H), 2.56 (t, 4H, J=7.26 Hz), 1.45-1.60 (m, 4H), 1.15-1.28 (m, 20H), 0.96 (s, 6H), 0.75-0.85 (m, 6H)). $^{13}$C NMR (CDCl$_3$, 200 MHz, ppm). δ: 142.28, 141.89, 141.16, 138.35, 136.26, 129.83, 122.70, 120.54, 119.34, 72.43 (2OCH$_2$), 32.05 (2C), 31.86 (2C), 30.97, 30.86, 29.68 (Cq), 29.42, 29.68, 29.24, 29.21, 28.47, 28.31, 22.65 (2CH$_3$), 21.87 (2C), 14.06 (2C). C-boron not observed. IR (KBr, cm$^{-1}$): 3016 (w), 2956 (s), 2922 (s), 2854 (s), 1520 (w), 1536 (w), 1476 (m), 1458 (m), 1416 (m), 1368 (m), 1380 (m), 1278 (s), 1268 (s), 1298 (s), 1250 (s), 1182 (w), 1108 (m), 1020 (w), 932 (w), 914 (s), 806 (w), 742 (s), 680 (w), 646 (m). Elemental analysis: calculated for C$_{31}$H$_{49}$BO$_2$S$_2$: C, 70.43%; H, 9.34%; S, 12.13%. Found: C, 70.79%; H, 9.66%; S, 12.24%.

General Procedure for the Preparation of the Tin Precursor

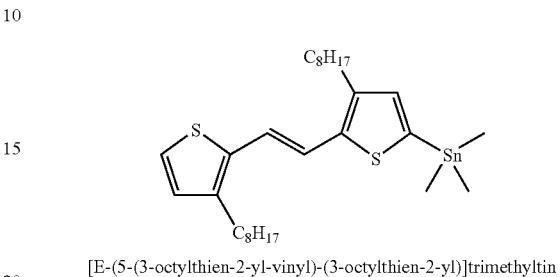

[E-(5-(3-octylthien-2-yl-vinyl)-(3-octylthien-2-yl)]trimethyltin

A solution of (E)-1,2-bis(3-octylthien-2-yl)ethylene (1.15 g, 2.76 mmol) in dry THF (20 ml) was cooled to −78° C. and 1.9 ml (3.3 mmol, 1.1 eq.) of a solution of n-BuLi in hexane (1.6M) were slowly added.

The solution was allowed to warm up again to −45° C. and, after stirring for 50 minutes, the reddish solution was subsequently cooled to −78° C. At this stage, a solution of trimethyltin chloride (606 mg, 3.03 mmol, 1.01 eq.) in 4 ml of dry THF was added. The solution immediately became orange and was then allowed to heat up again to ambient temperature. The solvent was removed and then the residue was extracted with diethyl ether and washed twice with sodium chloride solution. The organic phase was dried over MgSO$_4$ and, after evaporation of the solvent, 1.45 g of a dark orange oil were recovered. The $^1$H NMR analysis of this residual oil shows that it is a mixture of tin product (48%) and starting molecule (811 mg) (yield 51%). Due to the instability of the stannyl group during silica gel chromatography and the dangerous nature of the product, this mixture was used without more thorough purification in the Stille coupling reaction.

Synthesis of the Monomer TVF 2,7-Bis(5-[(E)-1,2-bis (3-octylthien-2-yl) ethylene])-fluoren-9-one. TVF

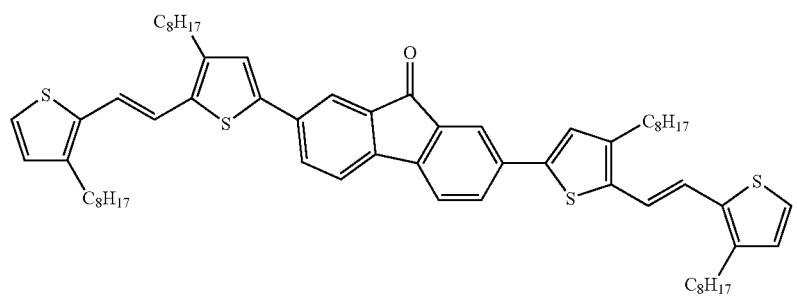

Synthesis from 5,5-dimethyl-2-[E-(5-(3-octylthien-2-yl-vinyl)-(3-octylthien-2-yl)][1,3,2]dioxoborinane (Suzuki Coupling)

183 mg of 2,7-dibromofluoren-9-one, 629 mg of 5,5-dimethyl-2-[E-(5-(3-octylthien-2-yl-vinyl)-(3-octylthien-2-yl)][1,3,2]dioxoborinane, 280 mg of K$_3$PO$_4$, 50 mg of Pd(P(Ph)$_3$)$_4$ and 12 ml of DMF were used.

The mixture was heated at 90° C. for 12 hours. After a standard treatment, the crude product was purified by column chromatography (silica gel, pentane/ether, 97:3) to give 960 mg (76.4%) of an oily orange product. After a standard treatment, the crude product was purified by column chromatography (silica gel, pentane/ether, 97:3) and then by a second column chromatography treatment using hexane/CHCl$_3$ (90:10) as eluent to give 81 mg (15%) of a dark orange waxy product.

Synthesis from [E-5-(3-octylthien-2-yl-vinyl)-(3-octylthien-2-yl)]trimethyltin (Stille Coupling)

215 mg of 2,7-dibromofluoren-9-one (0.63 mmol) and the mixture comprising the tin compound (1.40 mmol) were placed in anhydrous DMF (8 ml). The mixture was stirred under argon for 10 minutes and then 297 mg of K$_3$PO$_4$ (1.40 mmol) and 52 mg of Pd(P(Ph)$_3$)$_4$ (0.044 mmol) in 8 ml of DMF were added. The mixture was maintained at 95° C. with continual stirring for an additional period of time of 15 hours and then it was allowed to cool to ambient temperature. After a standard treatment, the crude product was purified by column chromatography (silica gel, pentane/ether, 95:5) to give 600 mg (93%) of a dark red waxy product.

$^1$H NMR (CDCl$_3$, 200 MHz, ppm): δ: 7.75 (d, 2H, J=1.34 Hz), 7.56 (dd, 2H, J=7.80 and 1.74 Hz), 7.34 (d, 2H, J=7.80 Hz), 7.05 (s, 2H), 7.01 (d, 2H, J=5.24 Hz), 6.90 (d, 4H, J=4.70 Hz), 6.78 (d, 2H, J=5.11 Hz), 2.59 (m, 8H, J=8.74 Hz), 1.60-1.48 (m, 8H), 1.30-1.18 (m, 40 H), 0.84-0.77 (m, 12H). $^{13}$C NMR (CDCl$_3$, 200 MHz, ppm): δ: 193.30 (C=O), 142.52 (2C), 142.07 (2C), 141.14 (2C), 139.28 (2C), 136.86 (2C), 136.86 (2C), 136.18 (2C), 135.08 (2C), 131.00 (2C), 129.88 (2C), 127.80 (2C), 126.38 (2C), 122.84 (2C), 120.95 (2C), 120.63 (2C), 119.82 (2C), 118.85 (2C), 31.89 (4C), 30.94 (4C), 30.78 (4C), 29.39 (4C), 29.25 (4C), 28.48 (4C), 22.66 (4C), 14.08 (4C). IR (KBr, cm$^{-1}$): 3066 (w), 3016 (m), 2954 (s), 2924 (s), 2852 (s), 1720 (s), 1600 (w), 1584 (w), 1542 (w), 1472 (s), 1464 (s), 1456 (s), 1436 (s), 1378 (w), 1294 (m), 1260 (m), 1086 (m), 1024 (m), 928 (s), 906 (m), 820 (s), 784 (s), 722 (m), 680 (w), 654 (w). Elemental analysis: calculated for C$_{65}$H$_{84}$OS$_4$: C, 77.33%; H, 8.39%; S, 12.70%. Found: C, 76.70%; H, 8.42%; S, 12.70%.

EXAMPLE 2

Synthesis of the Polymer PTVF

A solution of 260 mg of anhydrous ferric chloride in a mixture of solvents composed of 5 ml of nitromethane and 5 ml of chloroform was added dropwise to a solution of the comonomer (405 mg) in 15 ml of freshly distilled and degassed chloroform.

The addition was carried out at 0° C. with continual stirring over a period of time of 90 minutes. At the end of the addition, the mixture was reheated to 10° C. and was maintained at this temperature for a further 60 minutes.

The reaction mixture was then allowed to heat up again to ambient temperature and was stirred for 12 hours.

It was subsequently concentrated by evacuating under vacuum and then precipitated from 100 ml of methanol. The crude polymer was subsequently dissolved in 50 ml of chloroform and washed four times with a 0.1M aqueous ammonia solution (150 ml each time). In the following stage, the polymer was stirred for 48 hours with the same aqueous solution.

As synthesized, the polymer usually comprises small amounts of dopants of non unidentified chemical matrix and requires a further treatment for removal of the dopants.

The dopants were removed by washing the solution of the polymer in chloroform with an aqueous EDTA solution (0.05M, 200 ml).

The polymer was subsequently washed twice with water and then dried under vacuum.

EXAMPLE 3

Preparation of the Cell

The cell used for tests has the configuration represented in FIG. 2 and FIG. 4. It comprises a glass substrate covered with an ITO layer which is itself covered with two layers of PEDOT/PSS (conducting polymer) (product sold by BAYER).

The upper layer of PEDOT/PSS is covered with an active organic layer of the monomer, oligomer or polymer according to the invention (for example, TVF or PTVF) as a mixture with PCBM, which is a soluble fullerene derivative.

The active organic layer is finely coated successively with a layer of LiF and with a layer of aluminium.

The configuration of the cell is thus as follows:

Glass substrate/ITO/PEDOT-PSS/oligomer or polymer+PCBM/LiF-Al

The cell is prepared in the following way:

The surface area of the substrates is 4.25 cm$^2$.

Conditions for deposition by centrifugal coating (or spin coating):

In the first stage, the duration of the coating is 40 s at 1500 rev/min with an acceleration which makes it possible to achieve the 1500 revolutions in 4 s and then, in a second stage, the duration of the coating is 20 s at 2000 rev/min with an acceleration of 4 s to change from 1500 revolutions to 2000 revolutions.

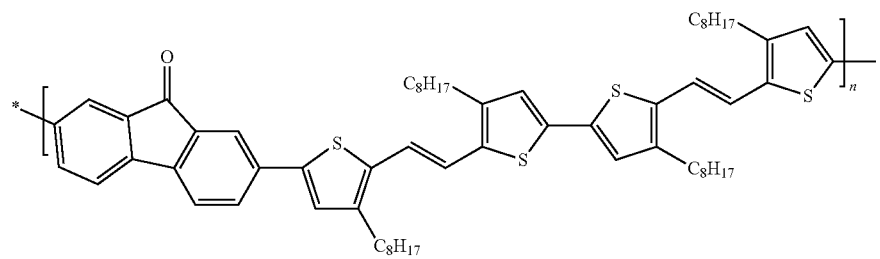

Stage 1: two successive layers of PEDOT/PSS (product sold by BAYER) are deposited with a spinner on the glass substrate covered with ITO. The thickness of the layer obtained is 80 nm. The deposited coat is produced in air and then dried under vacuum.

Stage 2: the active layer: PCBM (soluble fullerene derivative) and TVF mixture or PCBM and PTVF mixture, is deposited by spin coating.

The deposited coats are produced from a solution comprising: 10 mg of PCBM and 8.75 mg of TVF or PTVF in 1 ml of chlorobenzene. The deposited coat is produced under nitrogen in a glove box. The active surface area is 2 cm².

Stage 3: a layer of LiF (1.3 nm) is deposited under vacuum and then a layer of aluminium (70 nm) is deposited under vacuum. The surface area is approximately 0.3 cm².

EXAMPLE 4

Comparative

In this example, a cell is produced in the same way as in Example 3 with the only difference that the active layer is composed of a mixture of PCBM (acceptor) and of MDMO-PPV according to the document WO-Al-03/078498 instead of a mixture of PCBM and of TVF or PTVF.

EXAMPLE 5

Characterization of the Cells

The cell according to the invention prepared in Example 3 is then characterized in a glove box under a controlled atmosphere, namely an atmosphere of nitrogen with levels of oxygen and of water vapour of less than 1 ppm, at ambient temperature. The current-voltage (I(V)) characteristics are recorded under AM1.5 illumination at a power of 80 W/m².

The comparative cell comprising an active layer according to the prior art prepared in Example 4 is characterized in the same way.

Figure 1:
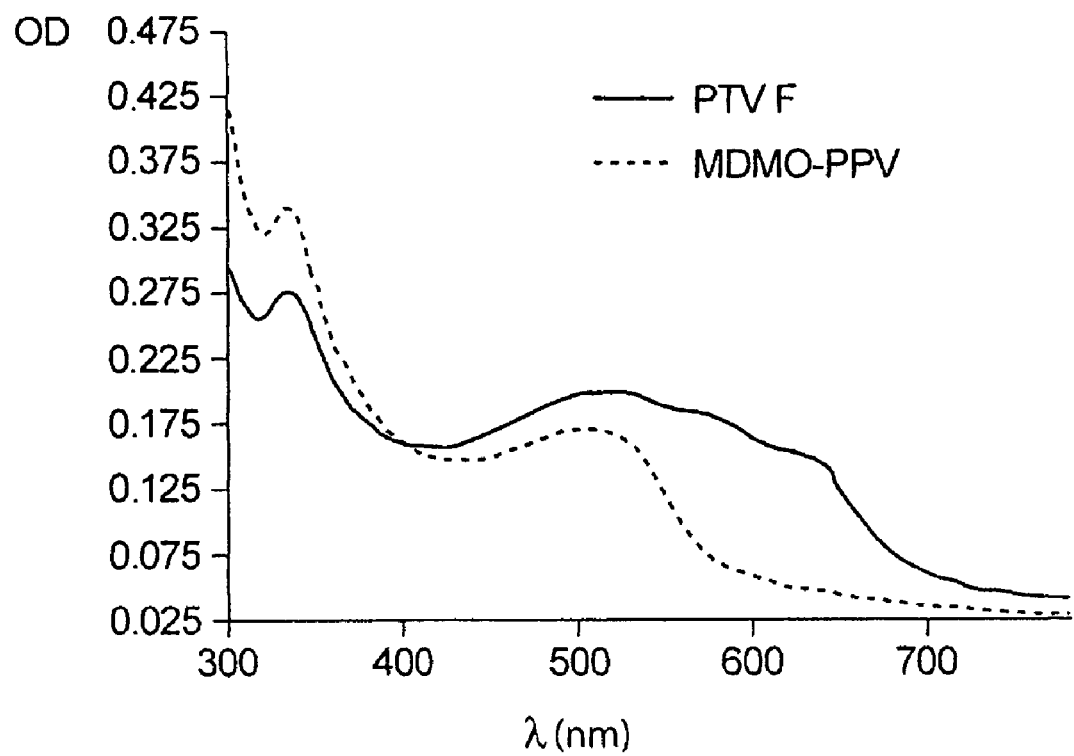
Figure 3:
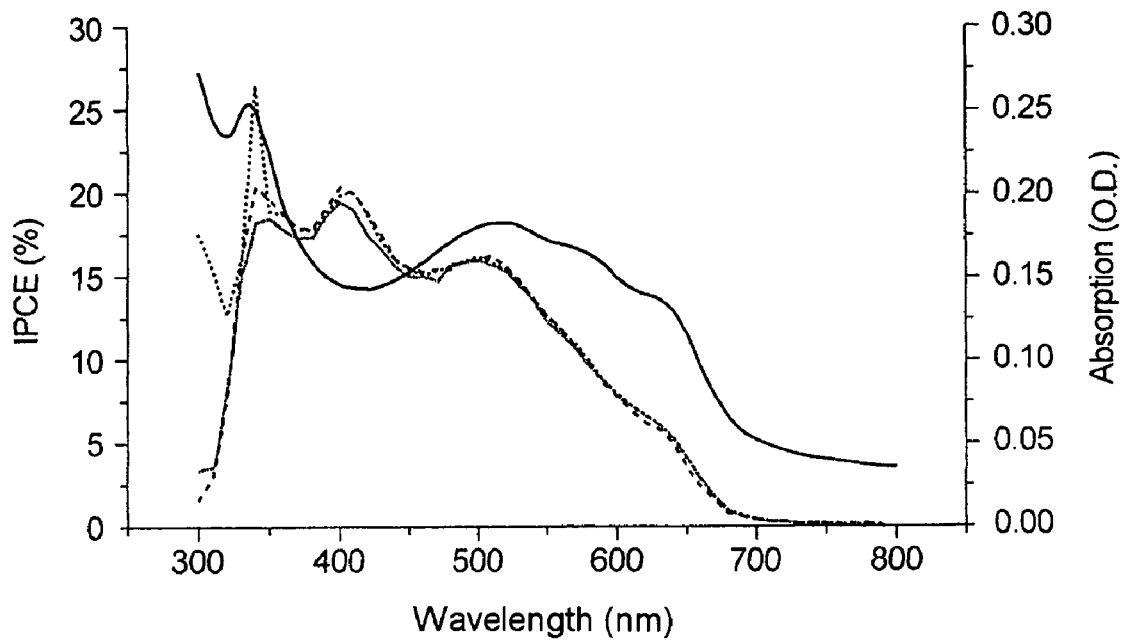
FIG. 3 is a graph which gives the action spectrum, namely the conversion efficiency as a function of the wavelength, of a cell based on PTVF (3 curves in different pointed lines for different operating conditions).

The characteristics of the cells with active layers according to the invention, prepared from the monomer TVF and the corresponding polymer PTVF, and active layers not in accordance with the invention, with a PCBM/MDMO-PPV mixture, are given in the following Table 1. The results of these tests and of others are presented in FIGS. 1, 3 and 5.

TABLE 1

|  | MDMO-PPV | TVF | PTVF |
|---|---|---|---|
| Isc (mA) | 1.42 | 0.76 | 1.01 |
| Jsc (mA/cm²) | 3.93 | 2.39 | 3.06 |
| Voc (V) | 0.70 | 0.70 | 0.50 |
| Pmax (mW/cm²) | 1.31 | 0.17 | 0.88 |
| FF | 0.43 | 0.32 | 0.58 |
| Eff. (%) | 1.47 | 0.66 | 1.10 |

Isc in mA corresponds to the short circuit current.

Jsc in mA/cm² corresponds to the short circuit current density.

Voc in V corresponds to the open circuit voltage.

Pmax corresponds to the maximum power density supplied by the cell (mW/cm²).

FF corresponds to the Fill Factor (corrective factor for the efficiency of the cell): ideally FF=1.

The efficiency corresponds to the degree of conversion of the photons to electrons.

The performances of the cells presented in Table 1 demonstrate the improvement in certain characteristics of the cells comprising the active layer according to the invention in comparison with the cells with an active layer comprising MDMO-PPV (WO 03/078498 A1) and which are tested under the same conditions as the compounds of the invention.

In particular, with PTVF, the cell exhibits a fill factor (FF) 1.3 times greater.

The rectifying property of the cell is better in the case of PTVF than for MDMO-PPV.

The monomer TVF, for its part, exhibits an open circuit voltage (Voc) equal to that determined for the MDMO-PPV polymer.

The invention claimed is:

1. Monomeric, oligomeric or polymeric compound corresponding to the following formula (I):

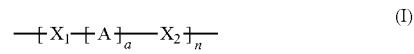

in which

A represents a polycyclic group optionally substituted by one or more identical or different R groups chosen from alkyl radicals, said polycyclic group comprising two rings chosen from aromatic carbon rings and/or aromatic heterocycles and comprising one group capable of making possible the attachment of a chromophoric group, $X_1$ and $X_2$, which are identical or different, each independently represent a group of formula (II):

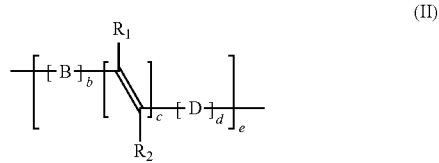

in which

B and D, which are identical or different, each independently represent an aromatic carbon ring or an aromatic heterocycle optionally substituted by one or more R groups;

$R_1$ and $R_2$, which are identical or different, each independently represent a group chosen from the hydrogen atom, R groups, the cyano group, the nitro group, halogen atoms and deuterium atoms;

b and d are integers from 1 to 100;

c is an integer from 1 to 20;

e is an integer from 1 to 100;

$X_1$ and/or $X_2$ are optionally substituted by one or more groups of formula (II) identical to or different from the substituted $X_1$ or $X_2$ group;

n is an integer from 1 to 1000;

a is an integer from 1 to 100;

one or more of the hydrogen atoms of the formula (I) can be replaced by a deuterium or fluorine atom, wherein the group capable of making possible the attachment of a chromophoric group is a group

where X represents O, S, Se or N—$R_3$, $R_3$ being chosen from the groups resulting from the reaction of a carbonyl group (X═O) with an amine to form an imine functional group;

wherein, in the formula (I), the polycyclic group of the A group is a condensed polycyclic group.

2. Compound according to claim 1, in which, in the formula (I), the A group is chosen from fluorenone, truxenone, indenofluorenone, benzofluorenone, dibenzofluorenone, indenofluorenedione, cyclopentafluorenone, cyclopentafluorenedione, thiopyranone, phenanthrenone or cyclopentadithiophenone groups; groups comprising a xanthone group of formula

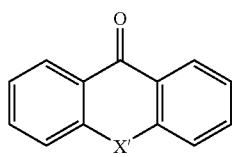

where X' represents a —CO—, —S—, —Se—, —NH—, —$CH_2$— or —$CH_2$═$CH_2$— radical; groups comprising a 4-piperidone group and two condensed aromatic carbon rings and/or aromatic heterocycles, these groups optionally being substituted by one or more R groups and/or optionally condensed with one or more aromatic carbon rings and/or aromatic heterocycles and the R groups being alkyl radicals.

3. Compound according to claim 1, in which, in the formula (II), B and D represent a thiophene.

4. Compound according to claim 1, in which B and D, when they represent a thiophene, are substituted by an alkyl radical of 1 to 10 carbon atoms.

5. Compound according to claim 1, which is a symmetrical monomer (n=1).

6. Compound according to claim 1, which is a regioregular alternating oligomer or polymer which preferably comprises a single type of A group and which is devoid of coupling defects.

7. Compound according to claim 1, in which the A group corresponds to the following formula:

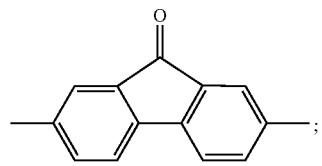

and $X_1$ and $X_2$, which are identical or different, correspond to the following formula:

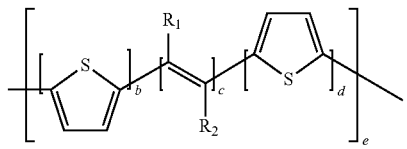

wherein the A group and the thienyl groups optionally are substituted by one or more R groups and the R groups are alkyl radicals.

8. Compound according to claim 1, corresponding to the following formula:

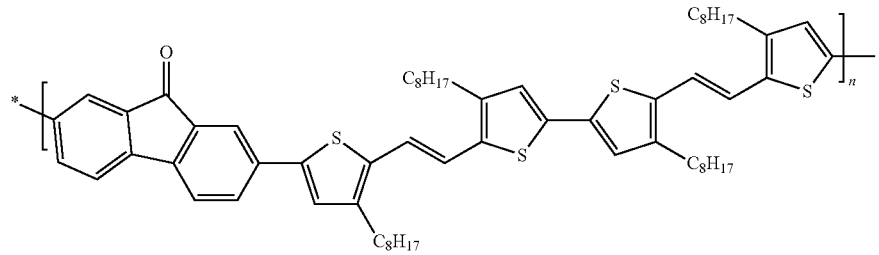

which is 2,7-bis(5-[(E)-1,2-bis(3-octylthien-2-yl)ethylene])-fluoren-9-one (TVF) if n=1; or poly(2,7-bis(5-[(E)-1,2-bis(3-octylthien-2-yl)ethylene])-fluoren-9-one) (poly(TVF)) wherein n is greater than 1.

9. An optoelectronic device comprising the compound according to claim 1.

10. The optoelectronic device according to claim 9, in which said optoelectronic device is a photovoltaic cell, a field-effect transistor or an electrochemical sensor.

11. Photovoltaic cell, comprising an active layer comprising an electron donor composed of the compound according to claim 1 and an electron acceptor.

12. Photovoltaic cell according to claim 11, in which said electron acceptor is chosen from organic acceptors and inorganic acceptors.

13. Compound according to claim 1, wherein b and d are integers from 1 to 12;

c is an integer from 1 to 5;

e is an integer from 1 to 10;

n is an integer from 1 to 200; and a is an integer from 1 to 5.

14. Compound according to claim 3, wherein, in the formula (II), B and D represent a thien-2,5-diyl group.

15. Compound according to claim 4, wherein the alkyl radical is an n-octyl radical.

16. Photovoltaic cell according to claim 12, wherein the organic acceptors are PCBM (1-(3-methoxycarbonyl)propyl-1-phenyl-[6,6]-C61), $C_{60}$, $C_{70}$, carbon nanotubes, perylene, tetracyanoquinodimethane (TCNQ) or quinoxalines; and inorganic acceptors are semiconductor nanocrystals.

17. Photovoltaic cell according to claim 16, wherein the semiconductor nanocrystals are coated by an organic layer.

* * * * *